United States Patent [19]

Hiller et al.

[11] 4,369,783

[45] Jan. 25, 1983

[54] DEVICE FOR THE PROPHYLACTIC OR THERAPEUTIC TREATMENT OF CATTLE

[75] Inventors: Dietrich Hiller, Wiesbaden; Peter Klatt, Kelkheim; Bernhard Reul, Königstein, all of Fed. Rep. of Germany

[73] Assignee: Hoechst Aktiengesellschaft, Frankfurt am Main, Fed. Rep. of Germany

[21] Appl. No.: 130,218

[22] Filed: Mar. 14, 1980

[30] Foreign Application Priority Data

Mar. 17, 1979 [DE] Fed. Rep. of Germany ....... 2910629

Jun. 29, 1979 [DE] Fed. Rep. of Germany ....... 2926283

[51] Int. Cl.³ .......... A61M 37/00

[52] U.S. Cl. .......... 128/260; 128/203.22; 128/213 R; 119/135

[58] Field of Search .......... 128/203.22, 206.11, 128/152, 201.18, 346, 342, 261, 262, 268, 207.19, 213 R, 253, 260; 119/135, 132, 130

[56] References Cited

U.S. PATENT DOCUMENTS

| | | | |
|---|---|---|---|
| 2,015,617 | 9/1935 | Claudius | 128/346 |
| 2,064,986 | 12/1936 | Mezz | 128/346 |
| 3,788,296 | 1/1974 | Klatt et al. | 128/268 |

FOREIGN PATENT DOCUMENTS

| | | | |
|---|---|---|---|
| 49187 | 3/1910 | Switzerland | 128/203.22 |

*Primary Examiner*—Henry J. Recla

*Attorney, Agent, or Firm*—Curtis, Morris & Safford

[57] ABSTRACT

Nose-clip for the prophylactic or therapeutic treatment of cattle, which comprises a bow whose ends are suitable for receiving active ingredients in the form of depot bodies, the receiving ends being either inclined towards each other and turned to face each other or the surfaces of the depot bodies being inclined towards each other and turned to face each other. The depot bodies may be divided into dimensionally stable, optionally elastic, applicators free from active ingredient, and dimensionally variable reservoirs containing the active ingredients, said reservoirs being connected with said applicators. The receiving ends and/or depot bodies may form an angle with the longitudinal axes of the ends of the bow.

13 Claims, 15 Drawing Figures

FIG. 4
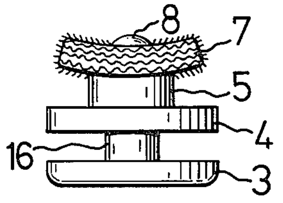
FIG. 5
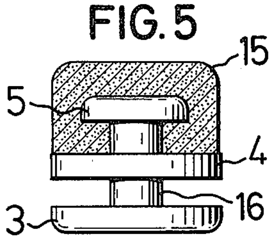
FIG. 6
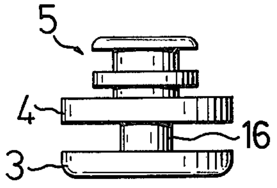
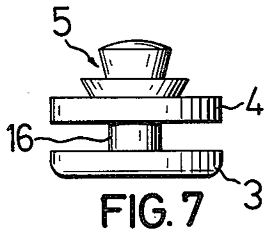
FIG. 7
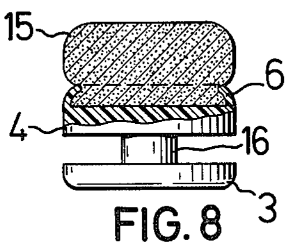
FIG. 8
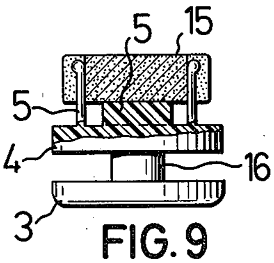
FIG. 9
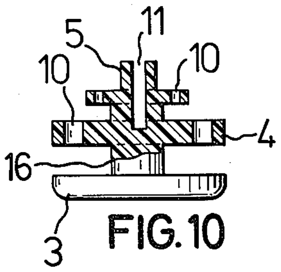
FIG. 10
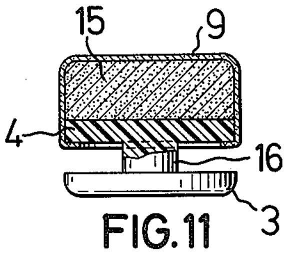
FIG. 11
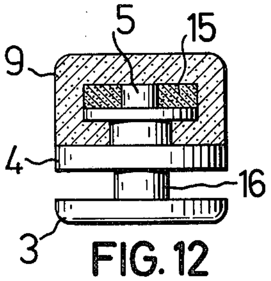
FIG. 12
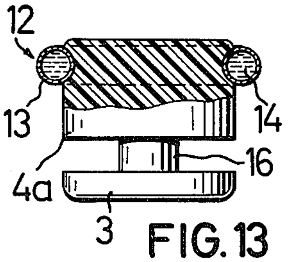
FIG. 13
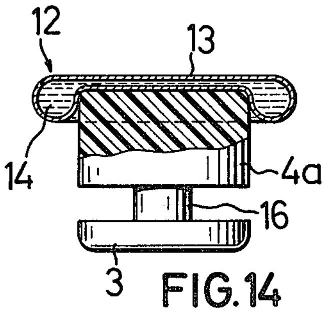
FIG. 14
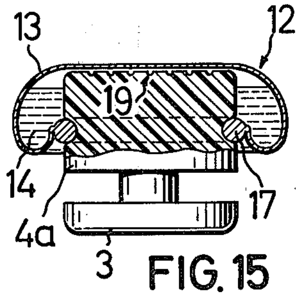
FIG. 15

DEVICE FOR THE PROPHYLACTIC OR THERAPEUTIC TREATMENT OF CATTLE

The present invention relates to nose-clips used for the administration of active ingredients in the prophylactic or therapeutic treatment of cattle.

In German Pat. No. 2,125,464 there are disclosed nose-clips, which enable medicaments to be administered to the nasal mucosa of animals over a prolonged period of time. In a preferred embodiment the end parts of the clip extend in parallel direction.

Wear tests with nose-clips, for example with those as described in said patent specification, carried out for several weeks to months and anatomical studies of the muzzle of cattle (for example of the muzzle of calves and grown-up cattle) showed that there was a need for particular embodiments of nose-clips for cattle to reach a better resorption, to completely prevent irritations of a nasal mucosa after prolonged wearing and to guarantee undisturbed application for the whole application period. The mucosa of the nasal septum in the nasal vestibule proved to be the most appropriate place of administration, particularly because it has a cavity.

It has now been found that a nose-clip consisting of a resilient, U-shaped element hereinafter named "bow", whose terminal parts are inclined towards each other and comprise means for receiving and administering active ingredients, is substantially adapted to the anatomic conditions at the place of administration, which is the mucosa of the nasal septum in the nasal vestibule, permits an improved resorption and provokes no pathological modifications at the place of administration after an application period of several weeks or longer.

It has moreover been found that the contact faces of the depot bodies (the active ingredients are present in the form of depot bodies) must form defined angles with the nasal mucosa.

The invention therefore relates to a nose-clip for the prophylactic or therapeutic treatment of cattle, which consists of a resilient, U-shaped bow whose ends are inclined towards each other and turned to face each other and are provided with means for receiving and administering active ingredients in the form of depot bodies. These are illustrated by way of example in the accompanying drawings and in the description referring to the drawings, in which FIG. 1 represents a view of a nose-clip as seen from below;

FIGS. 4 to 15 represent various embodiments of retaining members with and without depot bodies, and with applicators and reservoirs, respectively.

Figure 1:
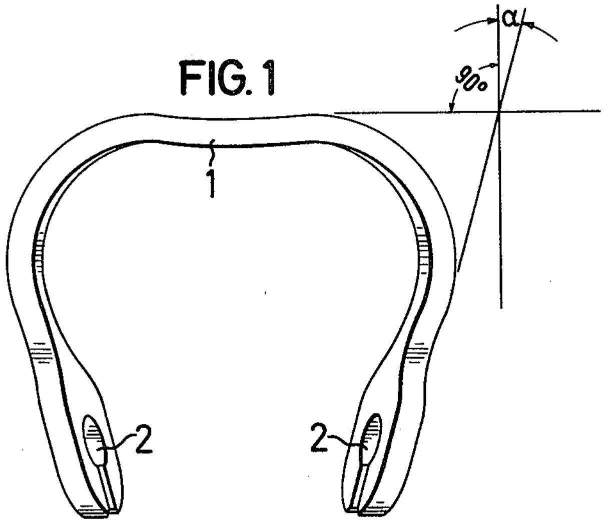
Figure 2:
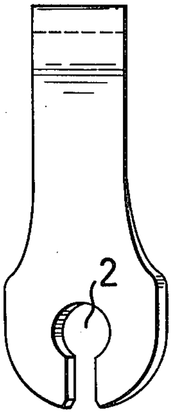
FIG. 2 represents a lateral view of a nose-clip.
Figure 3:
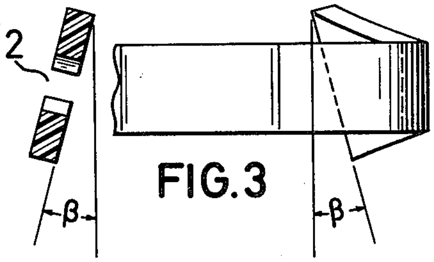
FIG. 3 represents a front view of a nose-clip, partly in cross-section.
Figure 18:
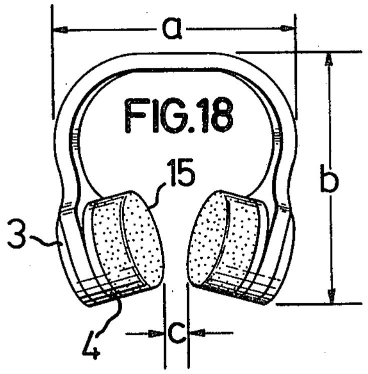
FIG. 18 represents a view of a nose-clip with depot body from below.
Figure 16:
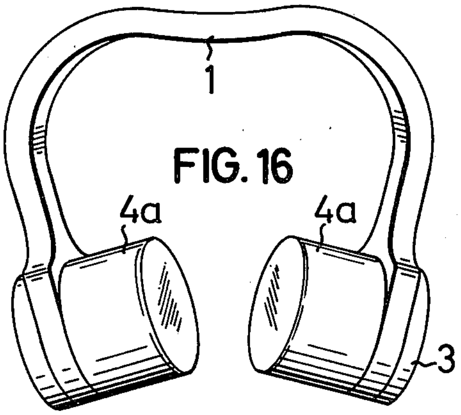
FIGS. 16 and 17 represent views from below of a nose-clip without reservoirs.
Figure 17:
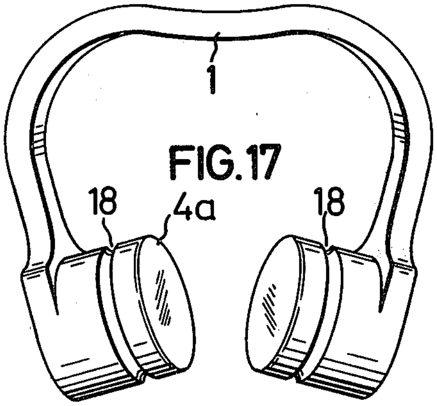

Referring now specifically to FIGS. 1, 2 and 3, the embodiment there shown comprises a bow portion 1 having terminal means, such as notches 2 for receiving retaining members capable of carrying active ingredients or medicaments in the form of depot bodies illustrated more specifically in FIGS. 4 to 15. The terminal means are shown in FIGS. 1 and 3 as inclined towards one another at an angle $\alpha$ that is greater than 0°, preferably between 5° and 30° and optionally between 10° and 23°, and turned to face one another at an angle $\beta$ which preferably ranges from 2° to 45°, most desirably between 8° and 28°. Alternatively, the faces of the depot bodies may be similarly inclined to one another and turned to face each other.

The strength of bow 1 of the nose-clip must be such that a correct anatomic seating of the depot bodies during the whole wear time is possible. On the other hand the elasticity of the bow 1 must be sufficiently high to permit an insertion and withdrawal of the nose-clip and to adapt to a certain degree to the growth, for example of a calf, during the wear time of the nose-clip.

The optimal force and relaxation occuring upon bending up the bow of 2.5 mm were determined by forcedistance measurements and by comparisons with the results obtained in wear tests with calves and grown cattle. A bow of a force from 0.5 N to 4, which is only little lower after the wear test, proved particularly appropriate. This force was determined on a material testing machine at a feed rate of 10 mm/min. on a distance of 2.5 mm, at a temperature of +21° C.

Suitable materials for the bow are metals or plastics, for example polyamide, polystyrene, especially polypropylene, and polyacetal (polyoxymethylene). The thickness of the bow varies within certain limits and depends inter alia on the material used.

Owing to the fact that said receiving or depot bodies form the angles $\alpha$ and $\beta$, an optimal adaptation of the nose-clip to the anatomic conditions in the nasal vestibule is made certain. Due to the torsion angle $\beta$ at the end of the low, mounting of the nose-clip and its insertion at the place of application are facilitated.

When the surfaces of the depot bodies mounted on said means are inclined towards each other and turned to face each other, said angles $\alpha$ and $\beta$ are formed by the depot bodies, i.e. said angles are formed due to particular forms of the depot bodies.

The nose-clip according to the invention is used for applying active ingredients over a prolonged period of time, for example for several weeks. Therefore the active ingredient is present in the form of depot bodies, said depot bodies consisting either of the active ingredient itself or of the active ingredient in conjunction with a carrier retarding the release of the active ingredient. The depot body may moreover be formed by the active ingredient in the form of a shaped structure, which is surrounded by a cover. It is also possible, of course, to administer active ingredients that are not present as depot bodies, by means of the nose-clip.

The depot bodies may be fixed directly on means 2. Preferably said means 2 are equipped with a retaining member 3, 4, 16, respectively (cf. FIGS. 4 to 12) for mounting the depot bodies on the end parts of the bow. The side of the retaining means that faces said means preferably has the configuration 3, 4, 16 shown in FIGS. 4 to 12. The diameter, the thickness and the form of the plate-shaped parts 3 and 4 of the retaining means do not have to be identical.

The embodiments according to the invention have the advantage that the depot bodies acting as pharmaceutical carriers of active ingredients may be prepared on the retaining means in a separate step or location, whereafter they may be mounted on means 2, if desired. This substantially facilitates an industrial-scale production.

A further advantage is that equal depot bodies and connecting parts may be mounted on nose-clips of different size and hence they may be used with cattle of different size. Moreover this embodiment of the nose-clip permits the use of two different depot bodies on a single clip. These depot bodies may differ in the active ingredients contained therein or in the release behavior of the same active ingredient, which enables, for example incompatible active ingredients to be separated from one another.

The retaining members may be mounted on the end parts 2 of the bow in various ways, for example by welding, by bonding, by a snap, in cup-like manner, by a bush-bottom system or by means of cylindrical or ball-and-socket joints. Suitably the ends of the bow have notches which form said means for retaining active ingredients, the retaining members being inserted in said notches. These notches may be off-centered so that their axes form an angle with the longitudinal axes of the end parts of the bow. Thus the bow and the retaining members may be connected in fixed manner or in freely movable manner, in the latter case the torsion angle being formed automatically.

A further advantage of the nose-clip according to the invention comprising a bow, means for taking up depot bodies and retaining members resides in the fact that the mechanical strain of the nasal mucosa is reduced when the bow and the retaining members are connected in freely movable manner.

The side of the retaining member, that is designated for receiving the depot body and which may also be present directly on means 2, may have various configurations, which depend especially on the properties and on the form of the depot body.

The depot bodies may be rigid, for example of plastics or waxes, or elastic, for example of silicone rubber, polyurethane rubber, polyacrylate rubber, natural rubber, butyl rubber. The retaining members and the depot bodies may be manufactured from the same material and in one step, provided that the material chosen has adequate properties. Otherwise the retaining members are manufactured first and the depot bodies are fixed thereupon subsequently. The bows and retaining members are manufactured from plastics by processes usual in plastics processing, while the depot bodies may be obtained by injection molding or other pharmaceutically usual processes such as casting and solidification or applying wax-like masses by compression, or by casting followed by cross-linking. The manufacturing processes used depend on the properties of the chosen materials and should permit an industrial-scale production as well as easy mounting of the retaining members and of the bows.

When depot bodies and retaining members are prepared from different materials at different times, the side of the retaining member that faces the depot body must be shaped such that it permits an anchoring of the depot body on the retaining member. This may be achieved by providing side 4 of the retaining member that faces the depot body, for example with a pin 5 (FIG. 4), that may have one or several grooves (FIGS. 5, 6, 7, 10, 12) or with several pins (FIG. 9) or by providing the border of this side shaped as a plate with an undercut (FIG. 8).

Depot bodies whose activity as a consequence of elution during their application is reduced or that suffer from erosion as a consequence of the release of active ingredient, may require mechanical strengthening. This may be achieved, for example by impregnation thereof in a non-woven fabric 7.

This non-woven fabric is fixed to pin 5 of the retaining member preferably by welding, riveting 8, nailing, srewing or bonding.

Further forms of the side of the retaining member that carries the depot body are illustrated in FIGS. 9–12. They permit the separate manufacture of the retaining member on which a prefabricated shaped article 15 is mounted, which latter is subsequently coated with a jacket 9 and optionally mounted on the retaining member (FIGS. 11 and 12). The retaining member may be coated completely or partially with the jacket 9 (FIGS. 11 and 12), which contributes to the depot effect. The depot bodies may alternatively be fixed directly on means 2 with a jacket of the above type, that may be made from an elastic material.

Depending on the casting technique used, the retaining member may be provided with holes 10 or slots 11 according to FIG. 10 to favor an escape of air when fixing the depot bodies on the retaining members by casting or injection molding or when inserting the retaining members.

The retaining members 3, 4, 16 may have, for example a circular, elliptical, tonsillar, oval, drop-like, oblong or reniform cross-section. The form chosen for the retaining members should be such that the depot bodies can be fixed thereon and are capable of forming the above-described angles to comply with the anatomic conditions in the nasal vestibule. Retaining members and/or depot bodies without circular cross-sections may form an angle with the longitudinal axis of the ends of the bow, as has been mentioned hereinbefore. By this arrangement an optimal anatomic seat is ensured and a confusion of the depot bodies is prevented.

The size of the retaining members and thus of the depot bodies depends on the weight of the animal and is preferably in the range from 15 to 25 mm diameter.

With depot bodies divided into a dimensionally stable, optionally elastic, applicator 4*a* free from active ingredient and into a dimensionally variable reservoir 12 that contains active ingredients, the applicator free from active ingredients acts as side 4 of the connecting part facing the depot body. With a view to its function, the applicator hence represents a further embodiment of side 4 of the retaining members (cf. numeral 4*a* in FIGS. 13 to 17 and numeral 4 in FIGS. 4 to 12 and 18). Hence the applicator can be considered as being part of the depot body and as being a further embodiment of side 4 of the retaining members.

In said embodiment the mechanical system of the nose-clip consists, for example, of bow 1, two retaining members 3, 16 and of two dimensionally stable applicators 4*a* (FIG. 16, numeral 16 not visible) free from active ingredients. The dimensionally stable applicators 4*a* free from active ingredients may likewise be positioned directly on the ends of the bow (FIG. 17), these ends being shaped themselves as dimensionally stable applicators 4*a* free from active ingredients. This has no influence on the formation of said angles. The size and the form of the dimensionally stable applicator free from active ingredients and of the reservoir containing active ingredients depend on the weight of the animal and are likewise in the range from 15 to 25 mm diameter.

The system free from active ingredients described hereinbefore is prepared preferably by injection molding.

The dimensionally flexible reservoirs 12 containing active ingredients are mounted on the dimensionally stable applicators 4*a* free from active ingredients and are of the membrane type, that is, the active ingredient or the active ingredients 14, optionally in the form of compositions containing active ingredients, are surrounded by a wall 13 free from active ingredients and represent hence the reservoir 12.

Reservoir 12 (depot) may have the form of an annular tube surrounding applicator 4*a* (FIG. 13) or of a pad (FIG. 14) or of a chamber mounted onto application 4*a* (FIG. 15).

The prefabricated tubes or pads have elastic walls 13 of 0.01 to 2.0, preferably 0.1 to 1.0, mm thickness and sufficient tensile strength. One side of the wall of the chamber is formed by applicator 4*a* (FIG. 15). The other sides of the chamber are formed by a prefabricated wall, as described hereinbefore. The latter may be cap-shaped and may possess an enlarged rim 17 (FIG. 15). This rim 17 may fit in a corresponding groove 18 (FIG. 17) of applicator 4*a*. This ensures a more secure mounting of reservoir 12 shaped for example as a tube or a chamber on the applicator. The surface of applicator 4*a* may have grooves 19 (FIG. 15) or bores facilitating the distribution of the active ingredient(s) or of preparations thereof 14 below wall 13. The active ingredient(s) or preparations are present as solids, liquids, gels, etc.

After having been charged with the active ingredient(s) or preparations thereof, the reservoir 12 is sealed liquid-tight in appropriate known manner, for example by welding or bonding and subsequent mounting on applicators 4*a*, or the reservoirs are charged subsequently.

A biopharmaceutical advantage of subdividing the depot bodies into a dimensionally stable part and into a dimensionally variable part resides in the fact that wall 13 of the part that contains the active ingredient(s) (reservoir) can be far thinner than with a depot body whose wall is part of the mechanical system and has to be thicker optionally for reasons of dimensional stability (numeral 9 in FIG. 12). A thinner wall permits easier diffusion and accordingly an easier and more complete release of active ingredients, which may be desirable depending on the purpose and on the nature of the treatment. The thickness and wall material chosen influence the release of active ingredient(s) in known manner.

Side wall may be made for example from silicone rubber or from copolymers of substituted ethylenes.

Contrary to a matrix-type part that contains active ingredients, the active ingredient(s)-containing contents (the active ingredient itself or a corresponding preparation) of the reservoir used is free from dimensionally stable polymers, which may be advantageous from a pharmaceutical and industrial point of view as regards the reproducibility and stability.

All the parts free from active ingredient(s) and optionally the active ingredient(s)-containing reservoir may be prefabricated and be mounted subsequently. Thus as great a liberty as possible is given for selecting appropriate materials both for the complete system free from active ingredient and for the active ingredient(s)-containing part of the nose-clip.

Due to the fact that the active ingredient-containing dimensionally flexible reservoirs, for example the abovespecified tubes, pads or chambers, have outstanding flexibility, they are capable of adapting themselves in outstanding manner not only to the dimensionally stable, optionally elastic, applicators free from active ingredient(s), but also to the anatomic conditions in the nasal vestibule.

Most desirably, the nose-clip is positioned directly adjoining the muzzle to hinder the animals from tearing the nose-clip out of their nose by rubbing against various objects. Consequently a nose-clip designed for calves has a smaller bow than a nose-clip designed for grown cattle. Moreover the retaining members suitably should have a smaller diameter with calves than with grown cattle.

A nose-clip designated for calves (FIG. 18), for example has a bow length a of from 35 to 45 mm and a leg depth b of from 20 to 35 mm, an angle $\alpha$ of 15° and an angle $\beta$ of 15°. The side of the retaining member that is designed for receiving the depot body has the form of a plate of 15 mm diameter, whereupon a depot body 15 is fixed. The distance c between the depot bodies ranges from 2 to 7 mm.

A nose-clip for grown cattle (FIG. 18) has a bow length a of from 55 to 70 mm, a leg depth b of from 40 to 55 mm, an angle $\alpha$ of 15° and an angle $\beta$ of 18°. The diameter of the plate of the retaining member amounts to 25 mm and the distance c between the depot bodies ranges from 10 to 20 mm.

A nose-clip for calves or cattle with subdivided depot bodies in general has corresponding dimensions.

What is claimed is:

1. A nose-clip for the prophylactic or therapeutic treatment of cattle, which comprises a bow portion the ends of which terminate in flattened surfaces provided with means for receiving active ingredients in the form of depot bodies, said bow portion being symmetrically shaped to lie in a first plane, each end of the bow portion and said receiving means being inclined towards each other to form an inclination angle $\alpha$ with respect to the symmetrical axis of said bow portion and turned in the same direction from said first plane to form a torsion angle $\beta$ with respect to a plane normal to said first plane thereby insuring that the surfaces of any depot bodies mounted thereon are inclined towards each other and turned to face each other for positioning in the nasal vestibules of cattle.

2. The nose-clip of claim 1 wherein said receiving means form an inclination angle $\alpha$ of from 5° to 30°.

3. The nose-clip of claim 1 wherein said receiving means form an inclination angle $\alpha$ of from 10° to 23°.

4. The nose-clip of claim 1 wherein said receiving means form a torsion angle $\beta$ of from 2° to 45°.

5. The nose-clip of claim 1 wherein said receiving means form a torsion angle $\beta$ of from 8° to 28°.

6. The nose-clip of claim 1 wherein said depot bodies are fixed directly onto said receiving means.

7. The nose-clip of claim 1, wherein the depot bodies are mounted onto the receiving means by retaining members cooperating with said receiving means and adapted to receive and hold said depot bodies.

8. The nose-clip of claim 6 or 7 wherein the depot bodies are mounted onto said receiving means or retaining members by a jacket which surrounds the depot body.

9. The nose-clip of claim 8 wherein said jacket is elastic.

10. The nose-clip of claim 1 wherein the depot bodies comprise a dimensionally stable applicator free from active ingredient and a dimensionally variable reservoir connected therewith and containing active ingredient.

11. The nose-clip of claim 10 wherein the reservoir is in the form of a tube or pad surrounded by an elastic wall.

12. The nose-clip of claim 10 wherein the reservoir comprises a chamber one wall of which is formed by said applicator with the remaining walls being elastic.

13. The nose-clip of claim 10 wherein said applicators are provided with grooves or holes to facilitate distribution of active ingredient therethrough.

* * * * *